(12) United States Patent
Quan et al.

(10) Patent No.: US 6,730,318 B2
(45) Date of Patent: *May 4, 2004

(54) TRANSDERMAL DELIVERY DEVICES CONTAINING POLYDIORGANOSILOXANE POLYMERS TO REGULATE ADHESIVE PROPERTIES

(75) Inventors: Danyi Quan, Salt Lake City, UT (US); Srinivasan Venkateshwaran, Salt Lake City, UT (US); Charles D. Ebert, Salt Lake City, UT (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,564

(22) Filed: Aug. 8, 2001

(65) Prior Publication Data

US 2002/0004064 A1 Jan. 10, 2002

Related U.S. Application Data

(63) Continuation of application No. 09/198,924, filed on Nov. 24, 1998, now abandoned.
(60) Provisional application No. 60/066,868, filed on Nov. 25, 1997.
(51) Int. Cl.$^7$ ................................................ A61F 13/02
(52) U.S. Cl. ........................ 424/448; 424/449; 424/486; 424/487
(58) Field of Search ................................ 424/448, 443, 424/444, 445, 447, 449, 78.02; 514/159, 23, 263, 359, 408, 423, 424, 428, 458, 474, 54, 553, 557, 561, 563, 579, 62, 725, 772, 772.2, 772.3, 772.4, 777, 783, 844, 848, 975

(56) References Cited

U.S. PATENT DOCUMENTS

| | | | | |
|---|---|---|---|---|
| 5,474,783 A | * | 12/1995 | Miranda et al. | ............ 424/448 |
| 5,656,286 A | * | 8/1997 | Miranda et al. | ............ 424/449 |
| 5,683,711 A | | 11/1997 | Fischer et al. | |

* cited by examiner

Primary Examiner—Thurman K. Page
Assistant Examiner—Frank Choi
(74) Attorney, Agent, or Firm—Thorpe North & Western, LLP

(57) ABSTRACT

The adhesive capability of matrix-type transdermal devices for the delivery of drugs, cosmetics, emollients and the like is altered by incorporating into the pressure-sensitive adhesive an effective amount of a polydiorganosiloxane polymer fluid adhesion adjusting agent. The properties of the pressure-sensitive adhesive are modified to enable a matrix-type patch to adhere temporarily to the skin for a period sufficient to accomplish its desired delivery purpose and then be removed without causing skin damage or irritation and without leaving substantial adhesive residue on the skin. Polydimethylsiloxanes (dimethicones) are preferred adhesion adjusting agents and acrylic-based polymers are preferred pressure-sensitive adhesives. Matrix-type patches containing anti-wrinkle agents formulated with dimethicones in the adhesive for application to areas on the face and particularly around the eyes are especially useful.

15 Claims, No Drawings

TRANSDERMAL DELIVERY DEVICES CONTAINING POLYDIORGANOSILOXANE POLYMERS TO REGULATE ADHESIVE PROPERTIES

This application is a continuation of U.S. Pat. Application Ser. No. 09/198,124 filed on Nov. 24, 1998, now abandoned, which claims priority to U.S. Provisional Pat. Application Serial No. 60/066,868 filed on Nov. 25, 1997 now abandoned.

This invention is directed to a method and composition for the alteration of the adhesiveness of pressure-sensitive adhesives used in transdermal delivery devices. Patch-type devices are well known for the transdermal administration of pharmaceutical agents as well as cosmetics, emollients and other skin treating agents. These patch-type devices are used for the administration of numerous classes of drugs or skin treating products. This invention is directed to a composition and method whereby the adhesiveness of the associated pressure sensitive adhesive of a transdermal delivery device is altered, rendering the device inherently less damaging to the skin of the patient than prior art patches.

Matrix-type transdermal delivery devices are designed to adhere to the skin for a period of time sufficient to allow administration of an active permeant or skin treating agent. Unfortunately, the adhesives in common use in transdermal devices often adhere too strongly to the area of application resulting in skin irritation or peeling of the skin layer when the patch is removed. The strength with which the device adheres to the skin is determined, to some extent, by the chemicals used and the molecular weight properties of the pressure sensitive adhesive.

The strength with which the device adheres to the skin is often touted as a beneficial attribute. This perspective is especially true where the device displays an ability to adhere strongly to the skin for extended periods of time. However, this adhesion tenacity is counter-productive if the removal of the device causes damage to the tissue to which it had been adhered. This is especially true where the device is a transdermal device which is adhered to sensitive tissue. This sensitive tissue may be, for example, an infected area in need of treatment, a preferred skin site for the administration of a type of drug to be transdermally delivered or a skin area which is inherently sensitive.

An infected skin site could be treated by a transdermal delivery system to administer an useful pharmaceutical agent directly to the infected tissue. Such treatment may be to compromised tissue to which an adhesive device will be bound and removal of the transdermal device could cause additional damage.

A preferred site of application is largely determined by the pharmaceutical agent, cosmetic, emollient, etc., that is administered. For example, a drug designed to alleviate an erectile dysfunction condition might need to be applied to the penis or nearby tissue. The application of an adhesive device to such sensitive tissue creates the ability of the adhesive to be removed easily and painlessly.

Moreover, transdermal treatment with emollients, cosmetics or bioactive agents has been found to be useful for the treatment of wrinkles. The treatment of wrinkles involves the adhesion of a transdermal device to a site, such as around the eye, for a short duration, such as overnight. Removal of adhesive patches from facial tissues and particularly around the eye is painful and can be emotionally traumatic. Following such treatment it would be useful for the device to be removed without causing additional dermal trauma or visible irritation.

Regardless of the application site, it would be desirous to have an adhesive combination which adheres effectively, but less strongly, than adhesives now known. It would be further desirous to have an adhesive for use in transdermal administration devices which facilitated both the transdermal delivery of the pharmaceutical or other bioactive agent and the facile removal of the device from the application site without the associated irritation, pain and trauma often caused by removal of pressure-sensitive adhesives.

One shortcoming of patch-type devices, particularly matrix devices in which the active agent is intimately dissolved or dispersed in the adhesive, involves the irritation caused to the skin secondary to removal of the adhesive device. The damage caused by strong adherence to the skin often involves substantial desquamation and ulceration upon removal of the device. Additionally, such devices cause substantial irritation of the adhered tissue during administration of the drug or other agent.

It would therefore be desirable to provide a transdermal device where the adhesive composition did not cause these undesirable irritations, desquamation and ulcerations.

OBJECTS OF THE INVENTION

It is therefore an object of the invention to provide a pressure-sensitive adhesive transdermal delivery device which upon removal following use, does not result in irritation, desquamation or ulceration of the treatment site.

It is another object of the invention to provide a pressure-sensitive adhesive transdermal delivery device which minimizes the damage caused to tissue secondary to the removal of the adhesive device.

It is still a further object of the invention to regulate the adhesive strength of a pressure sensitive adhesive patch.

SUMMARY OF THE INVENTION

These and other objects of the invention are accomplished through the incorporation of an adhesion-adjusting member, such as a polydiorganosiloxane polymer, intimately admixed with the pressure-sensitive adhesive portion of a matrix-type transdermal delivery device system. It has been discovered that the inclusion of a polydiorganosiloxane polymer into the adhesive portion of a pressure-sensitive adhesive device decreases the strength with which the adhesive adheres to the skin. Furthermore the intimate admixture of a suitable amount of a polydiorganosiloxane polymer member with the adhesive of a matrix-type pressure-sensitive adhesive device provides a device which is designed for short duration applications, such as overnight. In practice, the use of a polydiorganosiloxane polymer member as part of a pressure-sensitive adhesive formulation minimizes the damage caused by the adhesive secondary to the removal of the previously adhered device.

Polydiorganosiloxanes as a class may be utilized as more fully described below. Of that class the polydimethylsiloxanes are particularly preferred and are specifically exemplified. Polydimethylsiloxane polymers and copolymers are also known by the generic name dimethicone. These terms will be used interchangeably throughout this description.

One preferred embodiment is directed to the inclusion of a polydiorganosiloxane polymer into an adhesive formulation which is part of a pressure-sensitive matrix-type device for the treatment of wrinkles. In this matrix patch device the objective is to adhere the device to the skin area to be treated for an effective yet limited time. For example, this area might typically be the skin area around the eye where wrinkles traditionally develop incident to the aging process. After a desired period of time the transdermal device is removed by peeling the adhesive from the skin.

Also, as a result of transdermal administration, the treated skin is sensitive and more prone to irritation or damage. The removal of a patch, where the adhesive portion has been advantageously formulated using the siloxane polymer to adhere less strongly than pressure sensitive adhesives alone, is facile and painless. Where the pressure sensitive adhesives conventionally used in the art would damage and irritate the skin upon their removal, the modulated adhesive composition of this invention is easily removed without discomfort or damage to the underlying skin.

The following definitions will be useful in describing the invention and will eliminate the need for repetitive explanations.

By "transdermal" is meant transdermal or percutaneous administration of an active permeant for delivery through the skin for translocation or systemic delivery. Also, this term includes the application of a skin-treating composition directly to the skin area to be treated. To the extent that the invention can be utilized in the treatment of mucosal tissues they are also included in the term "transdermal." Hence the terms "skin," "derma," "epidermis," "mucosa," and the like shall also be used interchangeably unless specifically stated otherwise.

By the term "matrix," "matrix patch" or "matrix system" is meant the essential permeant or skin-treating components combined in a biocompatible pressure-sensitive adhesive which may or may not also contain other ingredients such as enhancers, anti-irritants, etc. A matrix system is usually an occlusive adhesive patch having an impermeable film backing and, before transdermal application, a release liner on the surface of the adhesive opposite the film backing.

By "pressure sensitive adhesive" is meant any biocompatible adhesive that can be used to secure a transdermal device to the skin surface. Representative of such pressure-sensitive adhesives are acrylic copolymers, rubber-based adhesives, ethylene vinyl acetate copolymers, latex polymers and waterborn acrylic copolymers. However, any other suitable pressure-sensitive adhesives may also be used which are compatible with polydiorganopolysiloxane polymer and the skin treating agents as utilized.

By "chemical agent," "drug," "permeant," "skin treating agent" and the like is meant any biotreating agent that can be delivered transdermally for any purpose. The agent may be selected from the group consisting of drugs, cosmetics, emollients, or other skin treating components. In some instances a chemical agent may be considered as belonging to more than one of the listed groups. For example, vitamins A and E or derivatives thereof may be combined with moisturizing agents, skin collagen synthesis promoting agents and exfoliating agents and the like as an emollient composition for the treatment of wrinkles but could also be considered as a cosmetic.

By "polydiorganosiloxane polymer" is meant a silicone fluid polymer having repeat units of the formula $R_2SiO_{2/2}$ siloxy units where R is a hydrocarbon or substituted hydrocarbon having from about 1 to 20 carbons atoms and is represented by the formula:

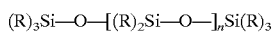

where R can be a hydrocarbon or substituted hydrocarbon of 1 to about 20 carbon atoms and can be selected from the group consisting of alkyl, aryl, cycloalkyl and the like which may be substituted to contain halogen, amino, hydroxy, ether or other similar functionalities. The integer "n" is sufficient to cause the silicone fluid to have a viscosity of between about 20 and 25,000 centistokes. Preferably the viscosity will be between about 20 and 12,500 centistokes.

Polydiorganosiloxane polymer fluids may be generally classified as unmodified silicones, linear and cyclic volatile silicones, alkyl/alkoxy modified silicones, phenyl modified silicones, aminofunctionalized silicones, polyglucoside silicones and polyether functionalized silicones.

Within the various classes, the polydiorganosiloxane polymer fluids are represented by proprietary tradenames including a number which is generally, but not always, indicative of viscosity.

Representative proprietary polydiorganosiloxane follow.

Exemplary of unmodified silicone fluid polymers are Dimethicone and Dimethiconol available as SP 96®(20, 50–1000), Visasil®(5M–100M) and SF18(350) from Costec Inc. (Palatine, Ill.), Dow Corning® 200 and 225 fluids from Dow Corning Corporation (Midland, Mich.), DM 100–1000, AK 5-1MM, X-345 and F-1006 from Wacker Silicones Corporation (Adrian, Mich.) and Sentry Dimethicone NF from Whitco Corporation (Greenwich, Conn.).

Representative of linear and cyclic volatile silicones are Cyclomethicone (>4) available as SF 1173, SF 1202 and SF 1204 from Costec Inc., Dow Corning® 244, 145, 344 and 345 fluids from Dow Corning Corporation and CM 040 from Wacker Silicone Corporation; Dimethicone SF96® (5) from Costec Inc. and DM 1 plus from Wacker Silicones Corporation; and Hexamethyldisiloxane available as DM 0.65 from Wacker Silicones Corporation.

Typical of alkyl/alkoxy modified silicones include lauryl dimethicone available as Dow Corning® Q2-5200 from Dow Corning Corp, LDM 3107VP from Wacker Silicones Corp.; Cetyl dimethicone available as Dow Corning® 2502 from Dow Corning Corp. and DMC 3071 from Wacker Silicones Corp.; Stearyl dimethicone available as SF1632 from Costec, Inc., Dow Corning® 2504 from Dow Coming Corp., and E32 from Wacker Silicones Corporation.

Illustrative of phenyl modified silicones are Phenyltrimeticone which as available as SF 1550 from Costec Inc., Dow Corning® 556 fluid from Dow Corning Corporation and PDM 20, 100, 1000 from Wacker Silicones Corporation.

Aminofunctionalized silicones may be represented by Amodimethicone available as SM2658 from Costec, Inc., Dow Corning® 929 and 939 from Dow Corning Corp. and L650, 652 and ADM 6057E from Wacker Silicones Corporation; Trimethylsilylamodimethicone available as SF1708-D1, SM2101 and SM2115-D2 from Costec, Inc. Dow Corning® Q2-7224 and Q2-8220 from Dow Coming Corp. and L653, 655, 656 and ADM 3047E from Wacker Silicones Corporation.

Indicative of the class of silicone polyglucosides is Octyl Dimethicone Ethoxy Glucoside (SPG 128) from Wacker Silicones Corporation.

Polyether functionalized silicones are typified by Dimethicone Copolyol available as SF 1188 from Costec, Inc. Dow Coming® 2501, 3225C, Q2-5324 and Q2-5434 from Down Corning Corp. and DMC 6032 and Cetyl Dimethicone Copolyol available as CMC 3071 from Wacker Silicones Corporation.

The above listings are representative and any polydiorganosiloxane polymer fluid functional for use in adjusting the adhesive properties of a pressure sensitive adhesive may be utilized.

With reference to the above formula, preferably R is methyl and the diorganopolysiloxane is a dimethylpolysiloxane polymer generically known as dimethicone. Therefore the terms "polydimethylsiloxane" and "dimethicone" are used interchangeably and refer to the preferred diorganopolysiloxane polymer. Various grades or weights of dimethicone may be referred to in the examples under the trade name Dimethicone "XXX" where "XXX" is indicative commercially of the viscosity of the polysiloxane polymer.

The siloxane polymer fluid content or concentration to be combined in the pressure-sensitive adhesive may vary over a wide range as long as it effectively regulates or controls the degree of tackiness such that the adhesive retains the transdernal device on the skin of a subject for the desired period of time and yet allows for the efficient removal of the device with no or minimal skin irritation or damage. Generally speaking, the siloxane polymer content may vary between about 0.1 and 20% by weight of the entire pressure-sensitive adhesive layer and will preferably be between about 0.1 and 10% by weight. In other words, where bioactive permeants, skin treating products, anti irritants and other additives are combined in the pressure-sensitive adhesive, the siloxane polymer content will be 0.1 to 20% and preferably 0.1 to 10% by weight of the entire pressure-sensitive adhesive/siloxane polymer/other ingredients combination.

EXAMPLES OF DIMETHICONE/PRESSURE SENSITIVE ADHESIVE COMPOSITIONS

In reference to the preferred embodiment, polydimethylsiloxanes (dimethicones), are silicone oils consisting of a mixture of fully methylated linear siloxane polymers having the formula:

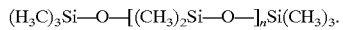

$(H_3C)_3Si-O-[(CH_3)_2Si-O-]_nSi(CH_3)_3$.

where n is an integer sufficient to provide a fluid having a viscosity that increases with degrees of polymerization, ranging from about 20 to 25,000 centistokes. They are widely used in the formulation of cosmetic and personal care products to protect, soothe or beautify the skin, hair and nails, especially to enhance the skin feeling and quality (softness and smoothness) but have not heretofore been known to moderate adhesive properties of pressure-sensitive adhesives.

The adhesion and tackiness for transdermal devices and particularly the matrix-type patches are very important factors, especially when the patches are applied to an area with sensitive skin, such as the face. The primary purpose of this invention is to use these silicone fluids as adhesive-altering agents in the pressure-sensitive adhesive of a matrix-type patch to control the tackiness and adhesiveness of the patch to the skin, making it easy to peel off the skin surface without causing damage or irritation.

Experiment Methods

The following illustrates the compounding of a dimethicone polymer into a pressure-sensitive adhesive and the testing of such dimethicone/adhesive combinations for relative adhesive properties.

The systems disclosed herein are made from the adhesive and varied amounts of a dimethicone polymer. Two parameters, tackiness and adhesion to steel, are used to evaluate the adhesion changes of the systems caused by adding different amounts of dimethicone to a pressure-sensitive adhesive. The methodologies of these two measurements are described below.

1. Matrix System Preparation

The solid content of adhesive is first determined by weighing a small amount of the adhesive solution in a pre-weighed aluminum dish. The solvent is evaporated by overnight drying in a convection oven maintained at 70° C. and the percent (%) solid content is determined based upon the weight of the dried adhesive. A known amount of the adhesive solution having the determined adhesive solids content is weighed into glass bottles. From the weight of the adhesive solution and the percent solid adhesive content, the amount of adhesive in the solution is calculated. Appropriate quantities of dimethicone are added to yield the desired dried film compositions. The glass bottle is then tightly capped, sealed with parafilm, and rotated overnight until all ingredients are completely dissolved and the solution is visually clear.

About 15 ml of a given adhesive/dimethicone solution is then dispensed on a release liner film, and cast with a 10 mil gap casting knife. This cast film is dried in a convection oven at 70° C. for 15 minutes to yield a dry film thickness of approximate 2 mil. A backing film is then laminated onto this adhesive film on the side opposite the release liner using a rubber roller. This matrix laminate is used to evaluate the adhesion of systems to be tested.

2. Tack

Tack is the ability of an adhesive to form a bond after brief contact with light pressure. It is the distinguishing characteristic of pressure sensitive adhesives which are often defined by the fact that they exhibit measurable tack (e.g. U.S. Pat. No. 3,769,254 to National Starch and Chemical Co.). Adhesives with a very high tack could form strong initial bonds with the skin upon application and thus may be difficult to remove.

The tack of adhesive formulations was measured by a TMI Probe Tack Tester (Model 80-02-01). In this apparatus a stainless-steel probe of 0.2 cm² area (37° C. temperature) is pressed into the adhesive surface with a pressure of 10 g/cm² for 1 second. The probe is then pulled away from the adhesive surface at a fixed rate of 1 cm/sec and the reported tack value (g) is the peak force of separation required.

3. Adhesion to Steel (Peel Adhesion)

Another typical test for measuring adhesive bond strength is the peel adhesion to steel. This test measures the force required to peel away a strip of adhesive from a rigid steel surface. Where a tack test measures the strength of adhesive bond formed after brief contact, a peel adhesion test is a measure of the bond strength after long contact. Therefore, peel adhesion might be a good predictor of the difficulty of removing a pressure sensitive patch at the end of its application time.

Peel adhesion was measured using an Instron Adhesion Tester (Model 1011) in which the adhesive formulation is peeled away from a steel surface at a 90° angle. The adhesives were affixed to a stainless steel plate for 5 minutes, then peeled away at a fixed rate of 12 inches per minute. The reported adhesion to steel value (g/inch) is the average force required to peel away the adhesive divided by the adhesive width perpendicular to the peel direction. A high adhesion to steel value is indicative of a stronger adhesive bond and thus an adhesive which would be more difficult to remove or peel off.

EXAMPLES

The following examples show representative formulations and results relating to tackiness and adhesion utilizing the tests described above.

Example I

A wear study was conducted using matrix-type patches made from Formulations A and B to compare the ease of removal following being worn overnight by the subjects to which the patches were applied. The combination of ingredients in this example are suitable for a matrix-type patch for the treatment or removal of wrinkles.

| | Composition (%, w/w) | |
|---|---|---|
| Formulation | A | B |
| DURO-TAK 87-2979* | 86.5 | 94.0 |
| Dimethicone 350** | 7.5 | 0.0 |
| Glycerin, USP | 5.0 | 5.0 |
| L-Ascorbic Acid 6-Palmitate | 0.5 | 0.5 |
| Vitamin E, USP | 0.5 | 0.5 |

*DURO-TAK 87-2979: Acrylic copolymer pressure sensitive adhesive;
**Dimethicone 350 (Polydimethylsiloxane having a viscosity of 350 cs.

Ten female volunteers, ages ranging from 30 to 60, applied the patches on their faces adjacent their eyes where crows feet develop and left them overnight. The evaluation graded the patches on ease of removal of patch, adhesive residue on the skin and irritation observed upon the patch removal. The scoring was made immediately after patch removal.

The results of the wear study show that both systems (A and B) adhered well to the skin. However, system A containing Dimethicone 350 was very easy to peel from the skin and left no significant adhesive residue on the skin. System B was more difficult to remove and left some adhesive residue on the skin.

Dimethicones (DMC) of different grades were formulated with the acrylic copolymer adhesive DuroTak 87-2979 ("2729") of Example I and the tackiness and adhesion to steel were measured by the above-mentioned methods in Examples II through V.

Example II

Dimethicone 350 was used in this example.

| Formulation | Composition (%, w/w) | Tackiness (g) | Adhesion to Steel (g/inch) |
|---|---|---|---|
| 2979/DMC 350 | 100/0 | 511 ± 41 | 1251 ± 105 |
| 2979/DMC 350 | 97.5/2.5 | 460 ± 29 | 1162 ± 60 |
| 2979/DMC 350 | 95.0/5.0 | 257 ± 7 | not available |
| 2979/DMC 350 | 90.0/10.0 | 240 ± 6 | not available |

The results show that tackiness decreases with increasing amounts of Dimethicone 350 in the system, indicating that by incorporating Dimethicone 350, a weaker bonding adhesive is formulated. In addition, the matrix system containing even 2.5% Dimethicone 350 shows a lower value of adhesion to steel, suggesting the less resistance to skin peel.

Example III

Dimethicone 200, which is a polydimethylsiloxane having a viscosity of 200 centistokes, was formulated with the adhesive in this example and the tackiness was measured.

| Formulation | Composition (%, w/w) | Tackiness (g) |
|---|---|---|
| 2979/DMC 200 | 100/0 | 511 ± 41 |
| 2979/DMC 200 | 95.0/5.0 | 477 ± 15 |
| 2979/DMC 200 | 92.5/7.5 | 440 ± 24 |
| 2979/DMC 200 | 90.0/10.0 | 353 ± 87 |

The results show that tackiness decreases with increasing amounts of Dimethicone 200 in the system, indicating that the incorporation of Dimethicone 200 into the adhesive lessens the degree of adhesive bonding to the skin thereby providing a less aggressive formulation.

Example IV

Dimethicone 100, which is a polydimethylsiloxane having a viscosity of 100 centistokes, was added to the adhesive and the tackiness was measured.

| Formulation | Composition (%, w/w) | Tackiness (g) |
|---|---|---|
| 2979/DMC 100 | 100/0 | 511 ± 41 |
| 2979/DMC 100 | 95.0/5.0 | 471 ± 30 |
| 2979/DMC 100 | 90.0/10.0 | 460 ± 80 |

The results show that tackiness decreases with increasing the amount of Dimethicone 100 in the adhesive system, indicating that the incorporation of Dimethicone 100 into the adhesive lessens the degree of adhesive bonding to the skin thereby providing a less aggressive formulation.

Example V

Dimethicone 20, which is a polydimethylsiloxane having a viscosity of 20 centistokes, formulated with the adhesive was also evaluated. Both tack and adhesion to steel were measured.

| Formulation | Composition (%, w/w) | Tackiness (g) | Adhesion to Steel (g/inch) |
|---|---|---|---|
| 2979/DMC 20 | 100/0 | 511 ± 41 | 1251 ± 105 |
| 2797/DMC 20 | 97.5/2.5 | 405 ± 82 | not available |
| 2979/DMC 20 | 95.0/5.0 | 329 ± 12 | not available |
| 2979/DMC 20 | 92.5/7.5 | 272 ± 16 | 1153 ± 93 |

The results show that tackiness decreases with increasing amounts of Dimethicone 20 in the adhesive system, indicating that incorporation of Dimethicone 20 into the adhesive lessens the degree of adhesive bonding to the skin thereby providing a less aggressive formulation. In addition, adding 7.5% Dimethicone 20 to the adhesive lead to a decrease in adhesion to steel, which is indicative of less resistance to skin peel.

Example VI

In this example another proprietary acrylic copolymer adhesive (TSR) was combined with Dimethicone 20 in different ratios to measure the change in the tackiness.

| Formulation | Composition (%, w/w) | Tackiness (g) | Adhesion to Steel (g/inch) |
|---|---|---|---|
| TSR/DMC 20 | 100/0 | 673 ± 7 | 1687 ± 77 |
| TSR/DMC 20 | 97.5/2.5 | 520 ± 30 | not available |
| TSR/DMC 20 | 95.0/5.0 | 417 ± 25 | 1370 ± 62 |
| TSR/DMC 20 | 90.0/10.0 | 353 ± 19 | not available |

Clearly, the above results show that Dimethicone 20 can significantly decrease the tackiness of TSR adhesive, and the tackiness decreases with the increase in the dimethicone content in the formulation. The results also show that, by adding Dimethicone 20, the value of adhesion to steel also decreased with increasing dimethicone content.

Examples VII to XIV illustrate formulations for the use of different adhesives. The dimethicone in these examples can be any grade such as illustrated in the previous examples.

Example VII

| Formulation | Composition (%, w/w) |
|---|---|
| DURO-TAK 87-2196 | 90–99.9 |
| Dimethicone | 0.1–10 |

Example VIII

| Formulation | Composition (%, w/w) |
|---|---|
| NACOR 72-9965* | 90–99.9 |
| Dimethicone | 0.1–10 |

*NACOR 72-9965: Waterborne acrylic copolymer pressure sensitive adhesive.

Example IX

| Formulation | Composition (%, w/w) |
|---|---|
| NACOR 72-8725* | 90–99.9 |
| Dimethicone | 0.1–10 |

*NACOR 72-8725: Waterborne rubber-based pressure sensitive adhesive

Example X

| Formulation | Composition (%, w/w) |
|---|---|
| DURO-TAK 36-6172* | 90–99.9 |
| Dimethicone | 0.1–10 |

*DURO-TAK 36-6172: Rubber-based pressure sensitive adhesive

Example XI

| Formulation | Composition (%, w/w) |
|---|---|
| DURO-TAK 34-4230* | 90–99.9 |
| Dimethicone | 0.1–10 |

*DURO-TAK 34-4230: Rubber-based hot melt pressure sensitive adhesive

Example XII

| Formulation | Composition (%, w/w) |
|---|---|
| PIB 500/Poly butyl 100 (34/36, % w/w)* | 90–99.9 |
| Dimethicone | 0.1–10 |

*PIB 500/Poly butyl 100: Polyisobutylene 500/Poly butyl 100 pressure sensitive adhesive.

Example XIII

| Formulation | Composition (%, w/w) |
|---|---|
| EVA-TAK 9663* | 90–99.9 |
| Dimethicone | 0.1–10 |

*EVA-TAK 9663: Waterborne ethylene vinyl acetate copolymer adhesive

Example XIV

| Formulation | Composition (%, w/w) |
|---|---|
| Robanb PS-20* | 90–99.9 |
| Dimethicone | 0.1–10 |

*Robanb PS-20: Water-based acrylic pressure sensitive adhesive.

These examples are not intended to be limiting in scope but are intended to be representative of formulations containing an added polydiorganosiloxane adhesion-altering member to a pressure-sensitive adhesive to cause the adhesive to be more easily removed. The invention is directed to any matrix-type transdermal delivery device held in place by a pressure-sensitive adhesive wherein the adhesive properties of the device may be altered or regulated by incorporating into the pressure-sensitive adhesive appropriate amounts of a diorganopolysiloxane polymer and is not directed to any particular chemical agent to be delivered or to any specific pressure-sensitive adhesive. The only limitation to the adhesive is that it must be biocompatible and functional when the siloxane polymer is combined therein.

What is claimed is:

1. A transdermal delivery device for delivering an effective amount of a chemical agent to the skin of a subject, comprising an impermeable backing layer, and a pressure-sensitive adhesive layer selected from the group consisting of: acrylic copolymers, water-borne acrylic copolymers, vinyl acetate copolymers, rubbers, and latex, wherein said pressure-sensitive adhesive layer contains an adhesion adjusting amount of a polydiorganosiloxane polymer fluid, having the formula $(R)_3Si-O-[(R)_2Si-O-]_nSi(R)_3$, wherein R is a hydrocarbon or substituted hydrocarbon of 1 to about 20 carbon atoms and n is an integer sufficient to cause said polydiorganosiloxane to have a viscosity of between about 20 and 25,000 centistokes, in order to provide said pressure-sensitive adhesive layer with a degree of tackiness of from about 236 g to about 501 g.

2. The device of claim 1, wherein the polydiorganosiloxane content is from about 0.1% to about 10% by weight of the pressure-sensitive adhesive layer.

3. The device of claim 1 wherein R is a member selected from the group consisting of alkyl, aryl, and cycloalkyl and, which are optionally substituted by a functional group selected from the group consisting of halogen, amino, hydroxy, and ether.

4. The device of claim 3 wherein R is methyl and said polydiorganosiloxane is fully methylated linear polydimethyl siloxane polymer having the formula:

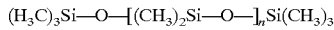

where n is an integer sufficient to cause said polydimethylsiloxane to have a viscosity of between about 20 and 25,000 centistokes.

5. The device of claim 4 wherein n is sufficient to cause said polydimethylsiloxane to have a viscosity of between about 20 and 12,500 centistokes.

6. The device of claim 1 wherein the chemical agent is a member selected from the group consisting of a drug, a cosmetic and an emollient.

7. The device of claim 1 wherein the pressure-sensitive adhesive is an acrylic copolymer.

8. The device of claim 1 wherein the pressure-sensitive adhesive is a water-borne acrylic copolymer.

9. The device of claim 1 wherein the pressure-sensitive adhesive is a rubber.

10. The device of claim 1 wherein the pressure-sensitive adhesive is a latex copolymer.

11. The device of claim 1, wherein the polydiorganosiloxane content is from about 0.1% to about 7.5% by weight of the pressure-sensitive adhesive layer.

12. The device of claim 1, wherein the polydiorganosiloxane content is from about 0.1% to about 5% by weight of the pressure-sensitive adhesive layer.

13. The device of claim 1, wherein the polydiorganosiloxane content is from about 0.1% to about 2.5% by weight of the pressure-sensitive adhesive layer.

14. The device of claim 1, wherein the degree of tackiness achieved is from about 272 g to about 460 g.

15. The device of claim 1, wherein the degree of tackiness achieved is from about 353 g to about 440 g.

* * * * *